(12) United States Patent
Beaty et al.

(10) Patent No.: US 10,684,245 B2
(45) Date of Patent: Jun. 16, 2020

(54) ELECTRODE ARRANGEMENTS FOR ELECTROCHEMICAL TEST ELEMENTS

(71) Applicant: Roche Diabetes Care, Inc., Indianapolis, IN (US)

(72) Inventors: Terry Beaty, Indianapolis, IN (US); Harvey Buck, Indianapolis, IN (US); Erica Diebold, Fishers, IN (US); Martin Gerber, Carmel, IN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 88 days.

(21) Appl. No.: 15/488,574

(22) Filed: Apr. 17, 2017

(65) Prior Publication Data
US 2017/0219510 A1    Aug. 3, 2017

Related U.S. Application Data

(63) Continuation of application No. PCT/US2015/058705, filed on Nov. 3, 2015.
(Continued)

(51) Int. Cl.
*G01N 27/327* (2006.01)
*C12Q 1/00* (2006.01)
(Continued)

(52) U.S. Cl.
CPC ......... *G01N 27/3272* (2013.01); *C12Q 1/006* (2013.01); *G01N 33/49* (2013.01); *G01N 33/66* (2013.01)

(58) Field of Classification Search
CPC .......... C12Q 1/00; C12Q 1/001; C12Q 1/004; C12Q 1/005; C12Q 1/006; C12Q 1/26;
(Continued)

(56) References Cited

U.S. PATENT DOCUMENTS

| 8,083,927 B2 | 12/2011 | Wang et al. |
| 8,992,750 B1 * | 3/2015 | Beaty ................. G01N 27/3272 |
| | | 204/194 |

(Continued)

FOREIGN PATENT DOCUMENTS

| EP | 2211170 A1 | 7/2010 |
| JP | 2013530408 A | 7/2013 |

(Continued)

OTHER PUBLICATIONS

PCT/US2015/058705; International Search Report and Written Opinion; dated Mar. 3, 2016.

*Primary Examiner* — Maris R Kessel

(57) ABSTRACT

Electrode arrangements for test elements, test elements and methods of determining sample sufficiency, monitoring fill time, establishing fill directions and/or confirming electrode coverage by a sample for test elements are disclosed. The test elements have an electrode-support substrate including a spacer having an edge defining a boundary of a capillary channel. The electrode-support substrate also includes a first electrode pair and a second electrode pair, wherein the first electrode pair is positioned between the second electrode pair. The method includes dosing the test sensor with the fluid sample; applying a signal to the first electrode pair and the second electrode pair, detecting a first response to the signal from the first electrode pair, and detecting a second response to the signal from the second electrode pair; determining a time period between the first response and the second response and then applying a measurement test sequence for an analyte of interest on the fluid sample if the time period is less than a first predetermined threshold.

5 Claims, 11 Drawing Sheets

Related U.S. Application Data

(60) Provisional application No. 62/074,352, filed on Nov. 3, 2014.

(51) Int. Cl.
   *G01N 33/49* (2006.01)
   *G01N 33/66* (2006.01)

(58) Field of Classification Search
   CPC . C12Q 1/34; C12Q 1/54; G01N 27/48; G01N 27/26; G01N 27/327–3274; G01N 33/487; G01N 33/49; G01N 33/66; A61B 5/14532; A61B 5/14535; A61B 5/14536
   See application file for complete search history.

(56) References Cited

U.S. PATENT DOCUMENTS

| | | | |
|---|---|---|---|
| 2002/0100684 A1* | 8/2002 | Bhullar | G01N 27/3272 204/403.01 |
| 2003/0203498 A1* | 10/2003 | Neel | C12Q 1/006 436/95 |
| 2004/0259180 A1 | 12/2004 | Burke et al. | |
| 2005/0016846 A1 | 1/2005 | Groll et al. | |
| 2005/0023152 A1 | 2/2005 | Surridge et al. | |
| 2007/0068807 A1* | 3/2007 | Feldman | A61B 5/14532 204/403.01 |
| 2007/0227911 A1 | 10/2007 | Wang | |
| 2008/0148873 A1* | 6/2008 | Wang | B01L 3/502715 73/864.73 |
| 2009/0240166 A1 | 9/2009 | Wang et al. | |
| 2010/0078322 A1* | 4/2010 | Yamanishi | G01N 27/3272 204/403.14 |
| 2011/0048940 A1* | 3/2011 | Wang | G01N 27/3272 204/403.14 |
| 2011/0186428 A1* | 8/2011 | Beaty | G01N 27/3272 204/403.01 |
| 2011/0236963 A1* | 9/2011 | Burke | G01N 27/3274 435/287.1 |
| 2013/0341186 A1 | 12/2013 | Hsu | |
| 2014/0216948 A1 | 8/2014 | McColl et al. | |
| 2014/0251833 A1 | 9/2014 | Smith et al. | |
| 2014/0291167 A1 | 10/2014 | Malecha | |

FOREIGN PATENT DOCUMENTS

| | | |
|---|---|---|
| WO | 2003091717 A1 | 11/2003 |
| WO | 2012003306 A1 | 1/2012 |
| WO | 2014/140161 A1 | 9/2014 |

\* cited by examiner

ELECTRODE ARRANGEMENTS FOR ELECTROCHEMICAL TEST ELEMENTS

CROSS-REFERENCE TO RELATED APPLICATIONS

This patent application is a continuation of Int'l Patent Application No. PCT/US2015/058705 (filed 3 Nov. 2015), which claims priority to and the benefit of U.S. Provisional Patent Application No. 62/074,352 (filed 3 Nov. 2014). Each patent application is incorporated herein by reference as if set forth in its entirety.

TECHNICAL FIELD

The disclosure relates generally to engineering and medicine, and more particularly to test elements, electrode arrangements for test elements, and methods of determining sample sufficiency, monitoring fill time, establishing fill direction, and confirming adequate electrode coverage by a sample for test elements.

BACKGROUND

Apparatuses and methods of testing biological fluids, as well as test elements for use in such apparatuses, are well known. For example, electrochemical testing methods are known that generally rely upon a correlation between a current (amperometry), a potential (potentiometry), or an accumulated charge (coulometry) and an analyte concentration, typically in conjunction with a reagent that produces charge-carriers when combined with the analyte. Known test elements for conducting electrochemical tests can be disposable test strips having a reagent that chemically reacts with the analyte of interest in a biological fluid sample. Generally, test elements are attached to or inserted into a test meter that can measure the reaction between the analyte and the reagent to determine the analyte concentration.

In general, test elements have a reaction zone containing measurement electrodes that directly contact the biological fluid sample. In some known amperometric and coulometric electrochemical measurement systems, the measurement electrodes are attached to electronic circuitry in the test meter that supplies an electrical potential to the measurement electrodes and measures the response of the electrochemical test element to this potential (e.g., current, impedance, charge, etc.). This response is proportional to the analyte concentration.

Robust monitoring and confirmation of fill of a capillary channel at the reaction zone is important for test elements with a capillary channel that is open on two or more sides. Such test elements have multiple direction filling capabilities since they may be dosed by the user along any open edge or at a corner. As such, fill location, sufficiency and time can vary depending on use variation by the user of the test element. Some known test elements, however, can give an inaccurate indication that a sufficient sample of the biological fluid has been obtained due to a progression of the biological fluid into, down or across the capillary channel of the test element. Such inaccurate indications can result in biased and/or inaccurate test results. Accordingly, a need exists for improved detecting, monitoring and confirming of the presence and progress of an adequate biological fluid sample volume for a successful analyte concentration or presence measurement by test elements.

BRIEF SUMMARY

The disclosure describes test elements with improved electrode arrangements, as well as methods of using the same for determining sample sufficiency, monitoring fill time, establishing fill direction, and/or confirming electrode coverage by a sample for test elements having sample chambers with multiple direction filling capabilities. The test elements and methods are based upon an inventive concept that includes not only a positioning, querying or interrogating but also a shaping of a secondary pair of electrodes around a primary pair of electrodes and then using the secondary pair of electrodes as alternative or supplemental counter electrodes (cathodes) and/or working electrodes (anodes) to the primary counter electrode or the primary working electrode. Advantageously, assignment of whether the electrodes are a working electrode, counter electrode, etc. is dynamic and thus not statically assigned. The inventive concept therefore provides certain advantages, effects, features and objects when compared to known electrode arrangements and methods of measuring an analyte concentration in a fluidic sample. For example, the methods allow for (1) improved sample sufficiency monitoring (e.g., inadequate volume or other dosing error), (2) sample fill time monitoring (e.g., unusual fill times), (3) sample fill direction monitoring (i.e., front, left side or right side), and/or (4) electrode coverage monitoring.

In one aspect, test elements are provided having a multiple, co-planar electrode arrangement. The test elements include an electrode-support substrate, a cover and a spacer. The electrode-support substrate includes first and second substrate side edges. The cover includes a cover first end and first and second cover side edges that substantially correspond to the first and second side edges of the electrode-support substrate. In some instances, at least the cover first end is offset from and extends a predetermined distance beyond the first end of the electrode-support substrate thereby defining an overhang portion (i.e., cantilevered). The cover may further include at least one discontinuity formed in the overhang portion to assist a user in dosing the test elements. A capillary channel is defined thereon at a first end of the electrode-support substrate and is open on two or more sides by the electrode-support substrate and the cover. The spacer may be attached to and positioned between the electrode-support substrate and the cover, with the spacer including an end edge defining a boundary of the capillary channel.

The test elements also include a first electrode pair provided within the capillary channel on the electrode-support substrate, and a second electrode pair provided within the capillary channel on the electrode-support substrate, where the first electrode pair is positioned between the second electrode pair (i.e., the second electrode pair surrounds the first electrode pair). An analyte-specific reagent is disposed at least over a portion of the first electrode pair in the capillary channel.

In some instances, the first electrode pair includes a first counter electrode and a first working electrode, and the second electrode pair includes a first and a second indicator electrode provided within the capillary channel on the electrode-support substrate, each of the first and second indicator electrodes being positioned along a respective side edge of the electrode-support substrate, where the first electrode pair is positioned between the first and second indicator electrodes.

In some instances, the second electrode pair is shaped at the first end to detect a convex fluid flow into the sample chamber. In other instances, the second electrode pair is shaped at the first end to detect a concave fluid flow into the sample chamber.

In view of the foregoing, methods are provided for measuring an analyte concentration in a fluid sample, such as a biological fluid sample, with a test element having the multiple, co-planar electrode arrangement as described herein. The methods include a step of providing a test element having an electrode-support substrate, a spacer coupled to the electrode-support substrate, the spacer including an edge defining a boundary of a capillary channel formed between a cover and the electrode-support substrate, a first electrode pair provided within the capillary channel on the electrode-support substrate, and a second electrode pair provided within the capillary channel on the electrode-support substrate, where the first electrode pair is positioned between the second electrode pair.

The methods also include a step of dosing the test element with the biological fluid sample, where the fluid sample flows into the capillary channel.

The methods also include applying a signal to the first electrode pair and the second electrode pair, either sequentially or simultaneously, detecting a first response to the signal from the first electrode pair, and detecting a second response to the signal from the second electrode pair.

The methods also include determining a time period between the first response and the second response, and applying a measurement test sequence for the analyte if the time period is less than a first predetermined threshold.

In another aspect, methods are provided for measuring an analyte concentration in a biological fluid sample with a test element having a multiple, co-planar electrode arrangement as described herein. The methods include a step of providing a test element having an electrode-support substrate, a spacer coupled to the electrode-support substrate, the spacer including an edge defining a boundary of a capillary channel formed between a cover and the electrode-support substrate, a first electrode pair provided within the capillary channel on the electrode-support substrate, the first electrode pair including a first counter electrode and a first working electrode, and a second electrode pair provided within the capillary channel on the electrode-support substrate, the second pair including a first and a second indicator electrode, with each of the first and second indicator electrodes being positioned along a respective side edge of the electrode-support substrate, where the first electrode pair is positioned between the second electrode pair.

The methods also include a step of dosing the test element with the biological fluid sample, where the fluid sample flows into the capillary channel.

The methods also include a step of applying a signal to (1) the counter electrode and the first indicator electrode, (2) the first electrode pair, and (3) the counter electrode and the second indicator electrode, where the counter electrode and the first indicator electrode are configured to transmit a first response, the first electrode pair is configured to transmit a second response, and the counter electrode and the second indicator electrode are configured to transmit a third response.

The methods also include detecting an initial response to the signal, where the initial response is a first one of the first, second and third responses detected, and detecting a final response to the signal, where the final response is the last one of the first, second and third responses detected.

The methods also include determining a time period between the initial response and the final response, and applying a measurement test sequence for the analyte if the time period is less than a first predetermined threshold. In some instances, the time period also includes the second response in the fill status/sufficiency decision.

In the methods, the primary electrode pair can be used to detect initial sample application to the capillary and to measure an analyte concentration. The secondary electrode pair can be used, interrogated or queried to determine whether adequate sample coverage of the primary electrode pair occurred, from which direction the sample flows, and how long after sample application it took to detect adequate sample application. The time from sample introduction to sample sufficiency may be measured and used to determine inadequate volume or to indicate dosing errors. Alternatively or additional, such time can be used as a parameter to modify the test sequence or algorithm to accommodate a slower fill time.

After confirming sample sufficiency, the secondary pair of electrodes may be disabled or may be used as anodes or cathodes to extend the primary working electrode's surface area or the counter electrode's surface area. Alternatively, one or both of the indicator electrodes of the secondary pair of electrodes can be interrogated as one or two secondary working electrodes to confirm a measured current density of the primary working electrode. In some instances, the measured current densities of the secondary pair of electrodes can be incorporated into an error alert (or failsafe) that detects irregularities in a vicinity of the primary working electrode such as electrode defects (e.g., cracks or voids), sample bubbles or inconsistencies, reagent irregularities or other conditions that may result in an inaccurate measurement of analyte concentration or presence.

These and other advantages, effects, features and objects of the inventive concept will become better understood from the description that follows. In the description, reference is made to the accompanying drawings, which form a part hereof and in which there is shown by way of illustration, not limitation, embodiments of the inventive concept.

BRIEF DESCRIPTION OF THE DRAWINGS

The advantages, effects, features and objects other than those set forth above will become more readily apparent when consideration is given to the detailed description below. Such detailed description makes reference to the following drawings, wherein:

FIGS. 18, 20 and 22) and concave sample flow (right column; FIGS. 19, 21 and 23) within a sample chamber of the exemplary electrode arrangements (top row; FIGS. 18 and 19) when compared to known straight indicator electrode arrangements (middle and bottom rows; FIGS. 20-21 and 22-23).

Corresponding reference characters indicate corresponding parts throughout the several views of the drawings.

Figure 1:
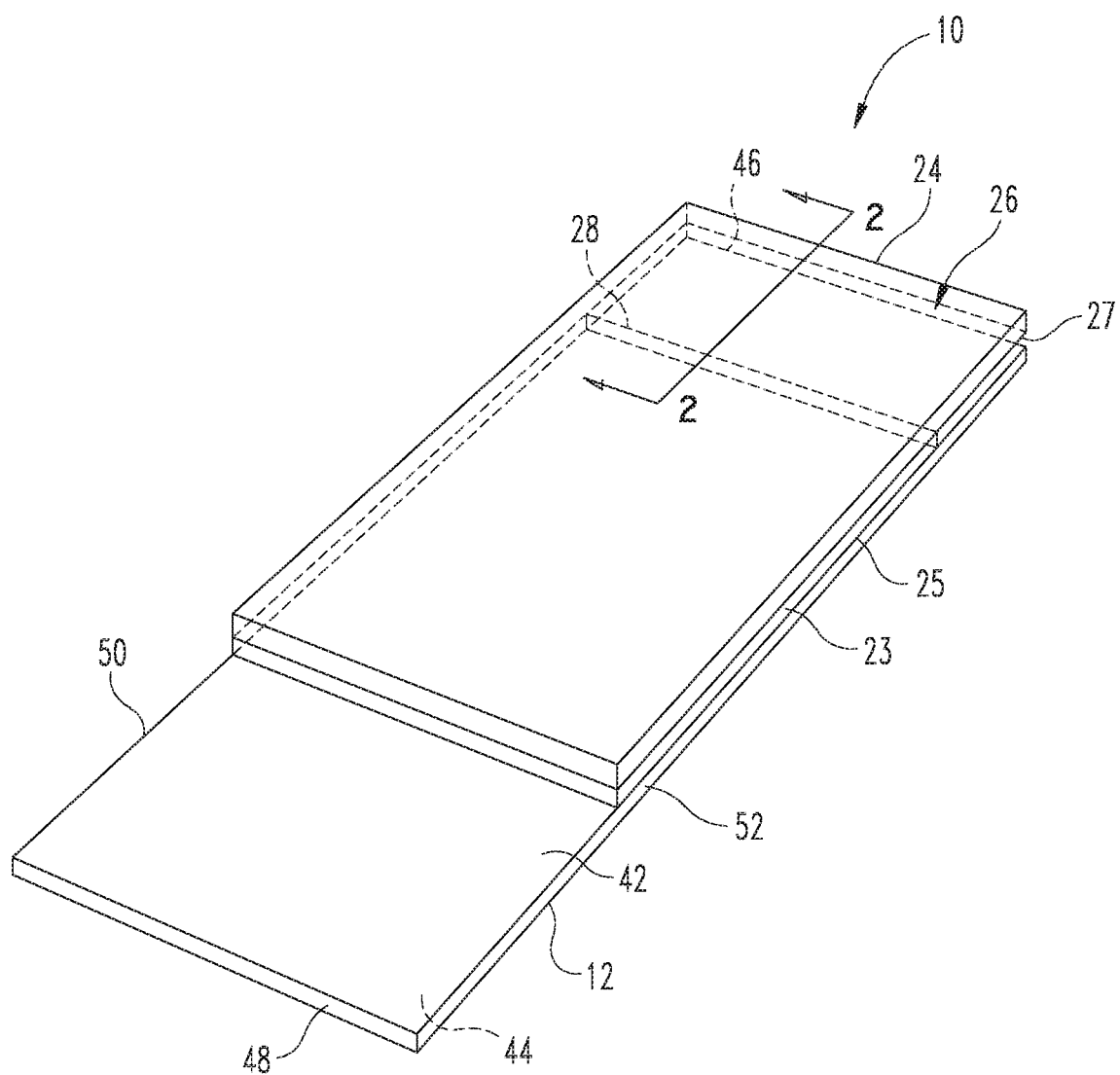
FIG. 1 is a perspective view of an exemplary test element.

While the inventive concept is susceptible to various modifications and alternative forms, exemplary embodiments thereof are shown by way of example in the drawings and are herein described in detail. It should be understood, however, that the description of exemplary embodiments that follows is not intended to limit the inventive concept to the particular forms disclosed, but on the contrary, the intention is to cover all advantages, effects, features and objects falling within the spirit and scope thereof as defined by the embodiments described herein and the claims below. Reference should therefore be made to the embodiments described herein and claims below for interpreting the scope of the inventive concept. As such, it should be noted that the embodiments described herein may have advantages, effects, features and objects useful in solving other problems.

DESCRIPTION OF EXEMPLARY EMBODIMENTS

The electrode arrangements, test elements and methods now will be described more fully hereinafter with reference to the accompanying drawings, in which some, but not all embodiments of the inventive concept are shown. Indeed, the electrode arrangements, test elements and methods may be embodied in many different forms and should not be construed as limited to the embodiments set forth herein; rather, these embodiments are provided so that this disclosure will satisfy applicable legal requirements.

Likewise, many modifications and other embodiments of the electrode arrangements, test elements and methods described herein will come to mind to one of skill in the art to which the disclosure pertains having the benefit of the teachings presented in the foregoing descriptions and the associated drawings. Therefore, it is to be understood that the electrode arrangements, test elements and methods are not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the disclosure pertains. Although any methods and materials similar to or equivalent to those described herein can be used in the practice or testing of the test elements and methods, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one." Likewise, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. For example, the expressions "A has B," "A comprises B" and "A includes B" may both refer to a situation in which, besides B, no other element is present in A (i.e., a situation in which A solely and exclusively consists of B) or to a situation in which, besides B, one or more further elements are present in A, such as element C, elements C and D, or even further elements.

Overview

Exemplary electrode arrangements, test elements and methods of use thereof are disclosed that use a multiple electrode arrangement of at least four co-planar electrodes arranged on a support substrate. The four co-planar electrodes can be arranged as two electrode pairs, where a first electrode pair is located between a second electrode pair. Briefly, a signal can be applied to various combinations of the four co-planar electrodes to obtain information regarding sample sufficiency, fill time, fill direction and/or electrode coverage by a sample for test elements having such an electrode arrangement.

Advantageously, the methods disclosed herein can be used with algorithms that deliver more accurate and reliable analyte concentration measurements and error alerts (or failsafes) during the use of various electrochemical measurement methods. If the error alert is triggered, an analyte concentration measuring device, apparatus or system can be configured to deliver an error code or an error message rather than an inaccurate analyte concentration. For example, the error alert could include direct messaging such as: "A conductive layer error in the test element was detected and thus an analyte concentration cannot be reported." or "A defect in the test element was detected and thus an analyte concentration measurement cannot be performed." This could result in a health care professional or user follow up to determine the cause and find a suitable device or test element that may not have this issue.

Details regarding exemplary electrochemical measurement methods that can be used in connection with the test elements described herein are disclosed in, for example, U.S. Pat. Nos. 4,008,448; 4,225,410; 4,233,029; 4,323,536; 4,891,319; 4,919,770; 4,963,814; 4,999,582; 4,999,632; 5,053,199; 5,108,564; 5,120,420; 5,122,244; 5,128,015; 5,243,516; 5,288,636; 5,352,351; 5,366,609; 5,385,846; 5,405,511; 5,413,690; 5,437,999; 5,438,271; 5,508,171; 5,526,111; 5,627,075; 5,628,890; 5,682,884; 5,727,548; 5,762,770; 5,858,691; 5,997,817; 6,004,441; 6,054,039; 6,254,736; 6,270,637; 6,645,368; 6,662,439; 7,073,246; 7,018,843; 7,018,848; 7,045,054; 7,115,362; 7,276,146; 7,276,147; 7,335,286; 7,338,639; 7,386,937; 7,390,667; 7,407,811; 7,429,865; 7,452,457; 7,488,601; 7,494,816; 7,545,148; 7,556,723; 7,569,126; 7,597,793; 7,638,033; 7,731,835; 7,751,864; 7,977,112; 7,981,363; 8,148,164; 8,298,828; 8,329,026; 8,377,707; and 8,420,404; as well as RE36268, RE42560, RE42924 and RE42953.

Electrode Arrangements, Test Elements and Methods of Use

Figure 2:
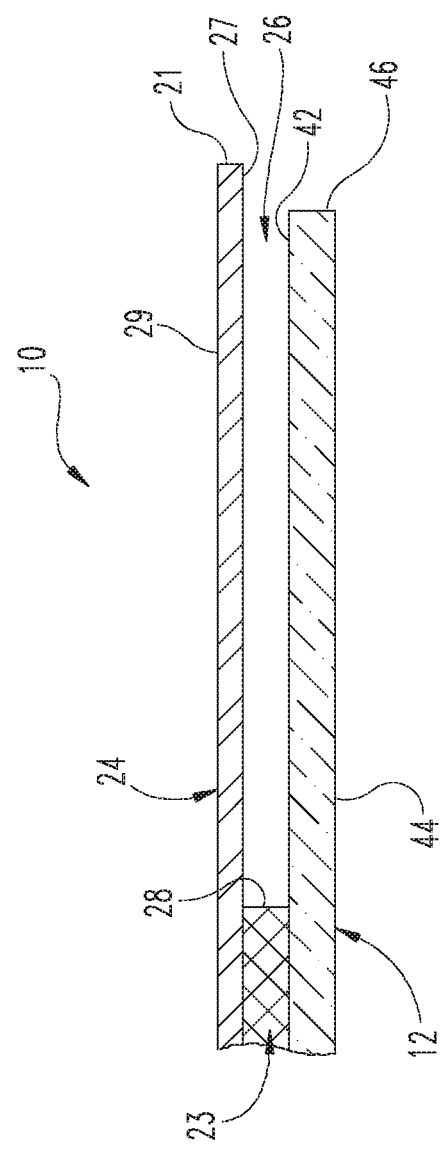
FIG. 2 is a section view of the test element of FIG. 1 taken along line 2-2.
Figure 3:
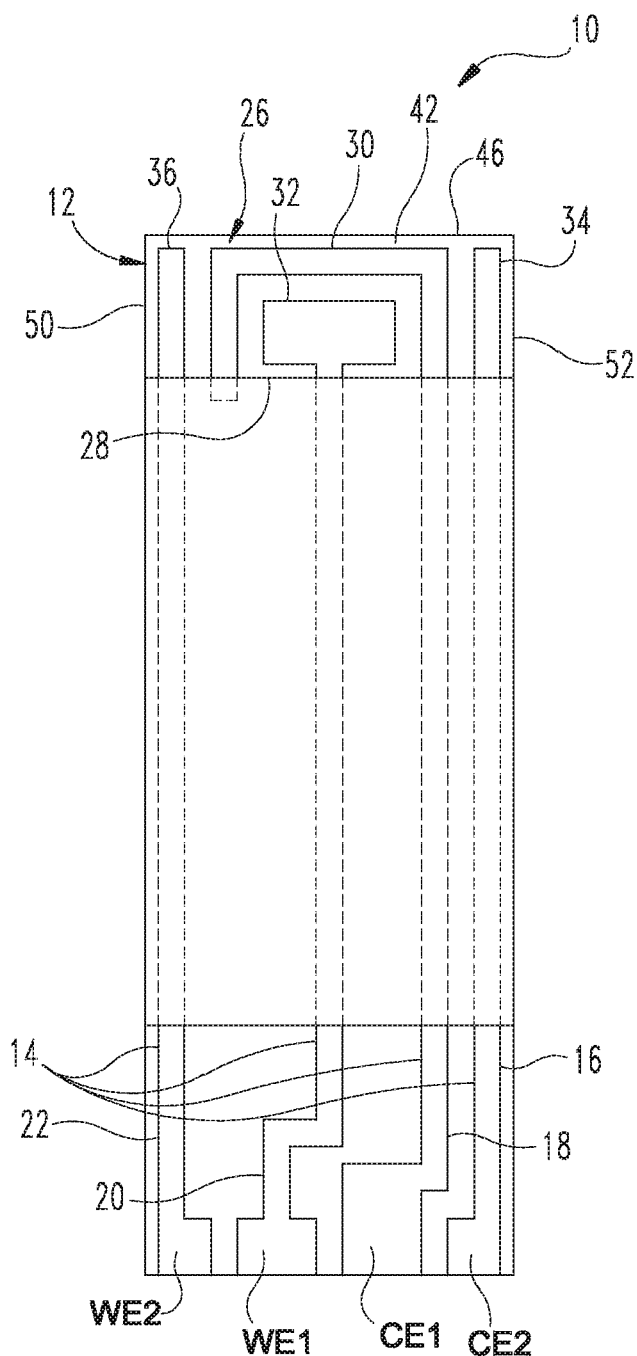
FIG. 3 is a plan view of the test element of FIG. 1 showing an exemplary electrode arrangement.

FIG. 1 is a perspective view of an exemplary test element 10. FIG. 2 is a section view of the test element 10 shown in FIG. 1 taken along line 2-2. FIG. 3 is a plan view of the test element 10 shown in FIG. 1.

Generally, the test element 10 has an electrode-support substrate 12, an electrical conductor 14 formed on the electrode-support substrate 12 that defines a plurality of electrode traces 16, 18, 20, and 22, a spacer 23 positioned on the electrode-support substrate 12, and a cover 24 positioned on the spacer 23. Alternatively, the electrical conductor 14 may form any number of electrode traces that enable the test element 10 to function as described herein. FIG. 2 shows that the cover 24 is positioned to provide a cantilever-based capillary channel design. In FIG. 3, the cover 24 is not shown for clarity.

As shown in FIGS. 1 and 2, the test element 10 is substantially rectangular (i.e., it has a length greater than its width, which is known as a test strip). Alternatively, the test element 10 can be provided in any one of a number of forms that enable the test element 10 to function as described herein. In addition, the test element 10 can be any one of a plurality produced from rolls of material, sheets of material, or any other material stock that enable the test element 10 to function as described herein. If a roll-to-roll process is used, the material selection for the fabrication of the test element 10 includes a material that is sufficiently flexible for roll processing, but is rigid enough to give a useful stiffness to the finished test element 10.

In some instances, the electrode-support substrate 12 of the test element 10 includes a first surface 42 facing the spacer 23 and a second surface 44 opposite the first surface 42. Furthermore, the electrode-support substrate 12 has opposite first and second ends 46, 48, and opposite side edges 50, 52 that extend between the first and second ends 46, 48. In one suitable embodiment, the electrode-support substrate 12 can be fabricated of a flexible polymer, for example, without limitation, a polyester or polyimide, such as polyethylene naphthalate (PEN) or polyethylene terephthalate (PET). Alternatively, the electrode-support substrate 12 can be fabricated from any other suitable materials that enable the electrode-support substrate 12 to function as described herein.

In some instances, the test element 10 is a full-width end dose ("FWED") test element having an inlet at the first end 46 of the electrode-support substrate. In a FWED test element, the spacer 23 extends between the opposite side edges 50, 52 of the electrode-support substrate 12. It is contemplated that the spacer 23 may be fabricated of a single component or a plurality of components. The spacer 23 includes an end edge 28 substantially parallel to and offset away from the first end 46 of the electrode-support substrate 12, and defining a boundary of a capillary channel 26 that extends across the entire width of the electrode-support substrate 12. Other suitable embodiments contemplate an end edge 28 that forms hemi-ovular, semi-circular, or other shaped capillary channels, and the one or more of the portions of end edge 28 may include linear or non-linear edges along all or part of its length (not shown). See also, US Patent Application Publication No. 2013/0140176.

The spacer 23 is fabricated from an insulative material, for example, without limitation, a flexible polymer including an adhesive-coated PET polyester. One particular non-limiting example of a suitable material includes a white PET film, both sides of which are coated with a pressure-sensitive adhesive. The spacer 23 may be constructed of a variety of materials and includes an inner surface 25 that may be coupled to the first surface 42 of the electrode-support substrate 12 using any one or a combination of a wide variety of commercially available adhesives. Additionally, the spacer 23 may be coupled to the electrode-support substrate 12 by welding, such as heat or ultrasonic welding. It also is contemplated that first surface 42 of the electrode-support substrate 12 may be printed with, for example, product labeling or instructions (not shown) for use of the test element 10.

Further, the cover 24 extends between the opposite side edges 50, 52 of the electrode-support substrate 12 and includes an end 21 that extends a predetermined distance beyond the first end 46 of the electrode-support substrate 12, thereby providing a cantilever-based capillary channel 26. See, e.g., U.S. Pat. No. 6,447,657. Alternatively, the end 21 of the cover 24 extends to the first end 46 of the electrode-support substrate 12 (i.e., end 21 and first end 46 are substantially coextensive). In some instances, the capillary channel 26 is therefore defined as the space between the cover 24 and the electrode-support substrate 12, bounded by the first end 46 and the opposite side edges 50, 52 of the electrode-support substrate 12 and the end edge 28 of the spacer 23.

The cover 24 is fabricated from an insulative material, for example, without limitation, a flexible polymer including an adhesive-coated PET-polyester, especially a transparent or translucent PET film. An advantage of using a transparent or translucent material is that a user can receive a visible indication that the capillary channel 26 is adequately filled. Moreover, the cover 24 may be constructed of a variety of materials and includes an upper surface 29 and a lower surface 27 that may be coupled to the spacer 23 using any one or a combination of a wide variety of commercially available adhesives. Additionally, the cover 24 may be coupled to the spacer 23 by welding, such as heat or ultrasonic welding.

In some instances, the cover 24 includes a non-leachable hydrophilic coating 31 (not shown) applied to the lower surface 27 to facilitate fluid transport into the capillary channel 26, and a hydrophobic coating 33 applied to the upper surface 29 to inhibit the fluid sample from flowing onto the test element's 10 external surface. The hydrophilic coating 31 is specifically chosen to impart a hydrophilic nature to the lower surface 27 of the cover 24 to encourage flow of the fluid sample, such as blood, into the capillary channel 26. The hydrophilic coating 31 can be chosen from many available coating materials designed to present a hydrophilic surface, for example, without limitation, polymeric substances that are composed of monomer building blocks of the same type or different types and have hydrophilic properties, including certain polyethers such as certain polyethylene glycols or certain polypropylene glycols, certain polysaccharides such as certain dextrans, certain polyalcohols such as certain polyvinyl alcohols, and certain polyether-polyurethane copolymers. Alternatively, the polymeric substances can be a surfactant- or detergent-doped polymer. The hydrophobic coating 33 is chosen to inhibit the fluid sample from flowing onto the upper surface 29 of the cover 24. Materials and methods for providing hydrophobic properties for a surface of a material are well known in the art. Likewise, one of skill in the art is familiar with selecting suitable materials having an untreated layer that is sufficiently hydrophilic or hydrophobic.

As shown in FIG. 3, the electrical conductor 14 forming the electrode traces 16, 18, 20 and 22 is provided on the first surface 42 of the electrode-support substrate 12, thereby forming a series of co-planar electrode traces. As used herein, "co-planar electrode traces" means electrode traces located on the same substrate surface (e.g., the first surface 42 of the electrode-support substrate 12). The electrical conductor 14 may be fabricated from, for example, without limitation, carbon (e.g., graphite, graphene), copper, gold, indium tin oxide, palladium, and platinum, as well as combinations thereof. In some instances, the electrode traces 16, 18, 20 and 22 are isolated from the rest of the electrical conductor 14 by laser ablation or laser scribing. The electrode traces 16, 18, 20 and 22 are fabricated by removing the electrical conductor 14 from an area extending around the electrodes either broadly, such as by broad field ablation, or minimally, such as by line scribing. Alternatively, the electrode traces 16, 18, 20 and 22 may be fabricated by other techniques such as, for example, without limitation, lamination, screen-printing, photolithography, etc.

In some instances, the four co-planar electrodes 30, 32, 34, 36 are arranged as a primary pair located between a secondary pair. The primary pair includes a first counter electrode 30 and a first working electrode 32. The secondary pair includes a second counter electrode 34 and a second working electrode 36. As described herein, electrode shape and configuration options enable determining sample sufficiency, monitoring of capillary channel fill time, and confirming electrode coverage by the sample. Sample sufficiency does not require that the capillary channel be completely filled, but rather that the electrodes being used are sufficiently covered with a sample.

In particular, the first counter electrode 30 and the first working electrode 32 are positioned in the capillary channel 26 and coupled to electrode traces 18 and 20, respectively. In addition, the test element 10 includes a second counter electrode 34 and a second working electrode 36 that are positioned in capillary channel 26 adjacent the edges 52 and 50 of the electrode-support substrate 12, respectively. The second counter electrode is coupled to electrode trace 16, and the second working electrode is coupled to electrode trace 22. As further shown in FIG. 3, the primary pair (i.e., first counter electrode 30 and first working electrode 32) is positioned between the secondary pair (i.e., second counter electrode 34 and second working electrode 36).

Additionally, the first counter electrode 30 is coupled to contact pad CE1 by electrode trace 18, and the first working electrode 32 is coupled to contact pad WE1 by electrode trace 20. Moreover, the second counter electrode 34 is coupled to contact pad CE2 by electrode trace 16, and the second working electrode 36 is coupled to contact pad WE2 by electrode trace 22. These contact pads provide a conductive area upon the test element 10 to be contacted by a connector contact of a test meter (not shown) once the test element 10 is inserted into the test meter. It is appreciated that the electrode arrangement shown in FIG. 3 is only a representation and that the configuration of the electrodes, the number of electrodes, as well as the spacing between the electrodes may vary in accordance with the disclosure and the test element 10 may include more or fewer than the number of electrodes illustrated herein. For example, without limitation, the first counter electrode 30 and the first working electrode 32 can be provided as substantially rectangular electrodes positioned laterally adjacent each other, or as electrodes having a plurality of "fingers" that cooperate to form an interdigitated electrode/interdigitated electrode array.

In some instances, test element 10 is a FWED test element, where the full width of first end 46 is open. As such, the capillary channel 26 is open on at least three sides including the first end 46 and a portion of both of the opposite side edges 50, 52 of the electrode-support substrate 12. The fluid sample can enter the capillary channel 26 generally longitudinally along any portion of first end 46 or generally laterally along any portion of the opposite side edges 50, 52 that define the capillary channel 26. Further, a corner can be used as the fluid sample entry point to the capillary channel 26 where the corner is defined as the point that the first end 46 meets one of the opposite side edges 50, 52. As discussed above, and further described herein, the electrodes' 30, 32, 34, 36 shape and configuration enables determining sample sufficiency, monitoring of the capillary channel 26 fill time, and confirming electrode coverage by the sample.

In some instances, the test element 10 is configured as a blood glucose test element and includes features and functionalities for electrochemically measuring glucose. In other instances, test element 10 is configured to electrochemically measure one or more other analytes such as, for example, amino acids, antibodies, bacteria, carbohydrates, drugs, lipids, markers, nucleic acids, peptides, proteins, toxins, viruses, and other analytes.

Figure 4:
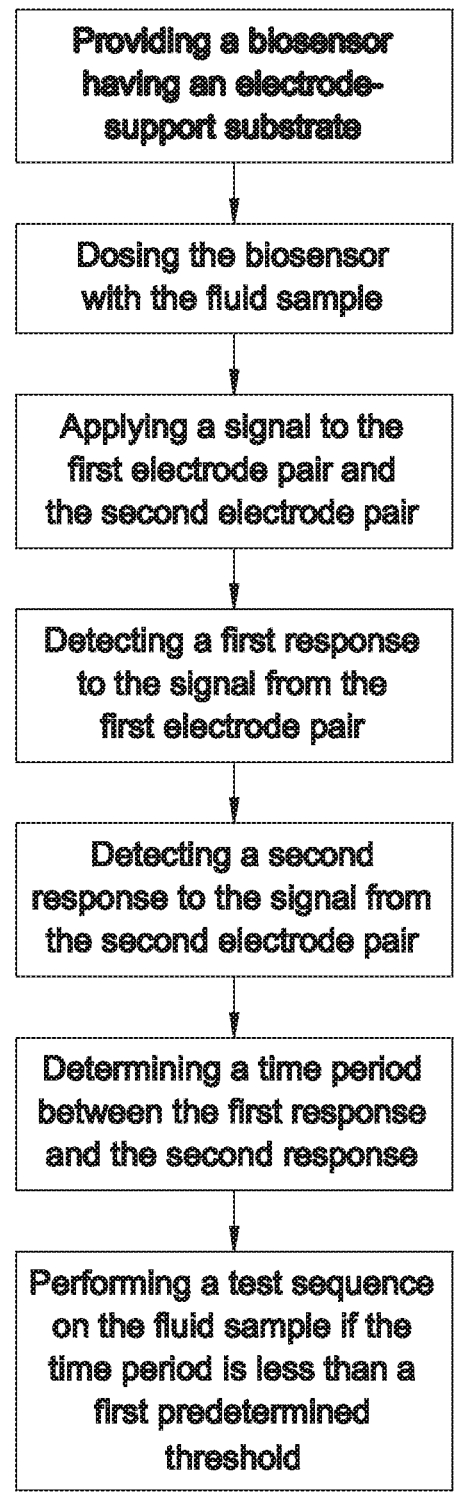
FIG. 4 is a flowchart of one exemplary method of using the test element of FIG. 1 and having the electrode arrangement of FIG. 3.

FIG. 4 is a flowchart of one suitable method 200 of using the test element 10 having the electrode arrangement shown in FIG. 3. Prior to introducing the fluid sample to the capillary channel 26, the test meter 202 or other device configured to use test element 10 applies a signal or test sequence, for example, without limitation, an AC signal and/or a DC signal, to the test element 10 to check for electrical continuity between the first counter and working electrodes 30, 32, and the second counter and working electrodes 34, 36. The signal or test sequence also can be used to check for electrode integrity or even electrode type.

In some instances, the fluid sample may be a biological fluid sample such as, for example, whole blood, plasma, serum, urine or saliva. In other instances, the fluid sample may be another type of sample to be tested for the presence or concentration of one or more electrochemically reactive analyte(s) such as an aqueous environmental sample.

Using the fluid sample, the test element 10 is dosed 204 from the first end 46 or one of the opposite side edges 50, 52. As the fluid sample expands or flows across the capillary channel 26, the test meter detects 206 a current between the first counter and working electrodes 30, 32 indicating that the fluid sample has bridged or contacted the two first electrodes. The test meter, using the secondary electrode pair 34, 36, detects 208 a current between the secondary electrode pair, thereby indicating that the fluid sample has bridged or contacted the two second electrodes.

Subsequent to the current indications between the primary electrode pair 30, 32 and the secondary electrode pair 34, 36, the test meter determines 210 the time period between the two indications and compares it to a first predetermined threshold. If the fluid sample sufficiency indication (i.e., the current indication between the secondary electrode pair 34, 36) occurs after the first predetermined threshold, the test meter may provide an error alert to the user and instructs the user to try again using a new test element 10. Alternatively, the test meter may provide a status update or prompt the user to apply more sample before providing the error alert and terminating the test. If the fluid sample sufficiency indication (i.e., the current indication between the secondary electrode pair 34, 36) occurs before the first predetermined threshold, the test meter executes an analyte test sequence 212. Thus, the measured time period between fluid sample introduction and fluid sample sufficiency may be used as a parameter to determine inadequate fill volume or to indicate dosing errors. Alternatively, based on the measured time period between fluid sample introduction and fluid sample sufficiency, if the first predetermined threshold is not met, but the time period exceeds a second predetermined threshold less than the first predetermined threshold, the meter may use the time period as a parameter to adjust or modify the analyte testing sequence or testing algorithm to accommodate a slower fill time.

Figure 5:
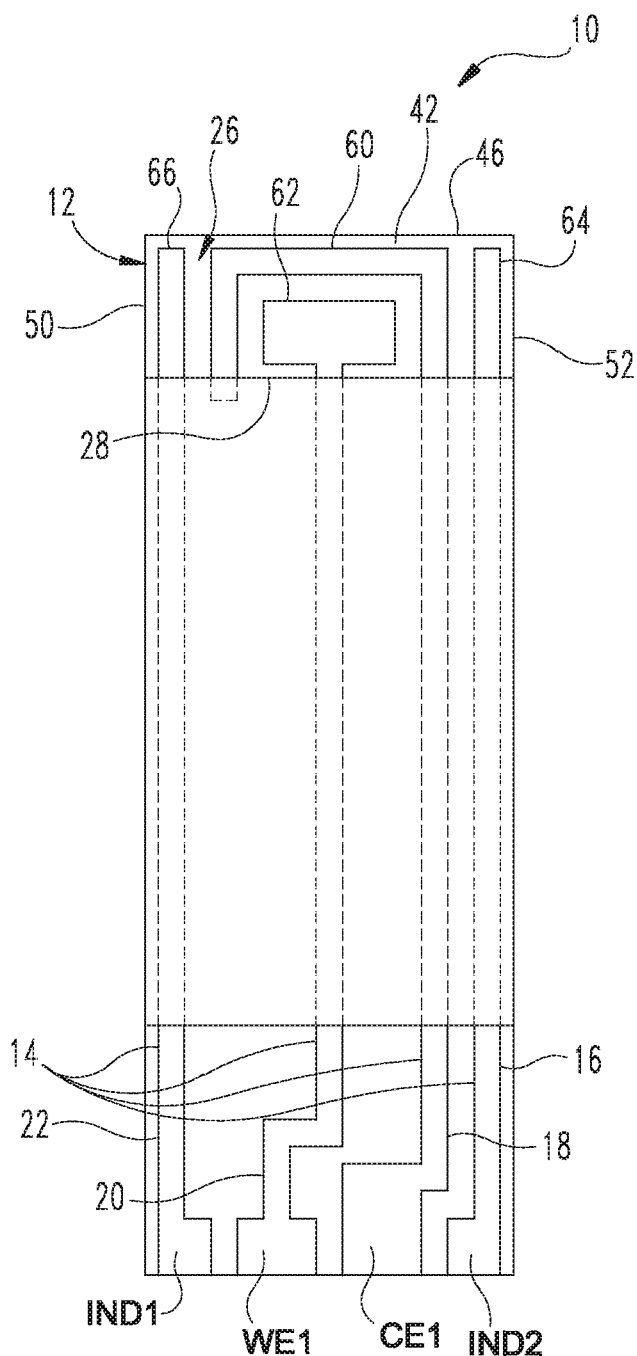
FIG. 5 is a plan view of an alternative electrode arrangement for use with the test element of FIG. 1.

FIG. 5 is a plan view of an alternative electrode arrangement for use with the test element 10 shown in FIG. 1. Four co-planar electrodes 60, 62, 64, 66 are arranged as a primary pair located between an outer electrode pair. The primary pair includes a first counter electrode 60 and a first working electrode 62. The outer electrode pair includes two co-function electrodes including a first indicator electrode 66 and a second indicator electrode 64. Here, each electrode of the outer electrode pair 64, 66 can function as both an indicator electrode and a working electrode or an additional counter electrode. As described herein, electrode shape and configuration options enable determining sample sufficiency, monitoring of capillary channel fill time, establishing fill direction of capillary channel 26 (e.g., sample dosing from front, right side, or left side), and confirming electrode coverage by the sample.

The first counter electrode 60 and the first working electrode 62 are positioned in the capillary channel 26 and are coupled to contact pad CE1 by electrode trace 18 and coupled to contact pad WE1 by electrode trace 20, respectively. Furthermore, the test element 10 includes a first indicator electrode 66 and a second indicator electrode 64 positioned in capillary channel 26 adjacent the edges 50 and 52 of the electrode-support substrate 12, respectively. The first indicator electrode 66 is coupled to contact pad IND1 by electrode trace 22 and the second indicator electrode 64 is coupled to contact pad IND2 by electrode trace 16. As shown in FIG. 5, the primary pair (first counter electrode 60 and first working electrode 62) is positioned between the outer electrode pair (first indicator electrode 64 and second indicator electrode 66).

The contact pads CE1, WE1, IND1 and IND2 provide a conductive area upon the test element 10 to be contacted by a connector contact of the test meter once the test element 10 is inserted into the test meter. It is appreciated that the electrode arrangement shown in FIG. 5 is only a representation and that the configuration of the electrodes, the number of electrodes, as well as the spacing between the electrodes may vary in accordance with the disclosure and the test element 10 may include more or fewer than the number of electrodes illustrated herein.

As described above, test element 10 is a FWED test element having the capillary channel 26 open on at least three sides including the first end 46 and a portion of both of the opposite side edges 50, 52 of the electrode-support substrate 12. The fluid sample can enter the capillary channel 26 generally longitudinally along any portion of first end 46 or generally laterally along any portion of the opposite side edges 50, 52 that define the capillary channel 26. Further, a corner can be used as the fluid sample entry point to the capillary channel 26 where the corner is defined as the point that the first end 46 meets one of the opposite side edges 50, 52. As discussed above, and further described herein, the shape and configuration of the electrodes 60, 62, 64, 66 enables determining sample sufficiency, monitoring of the capillary channel 26 fill time, establishing fill direction of the capillary channel 26 (e.g., sample dosing from front, right side, or left side), and confirming electrode coverage by the sample.

Figure 6:
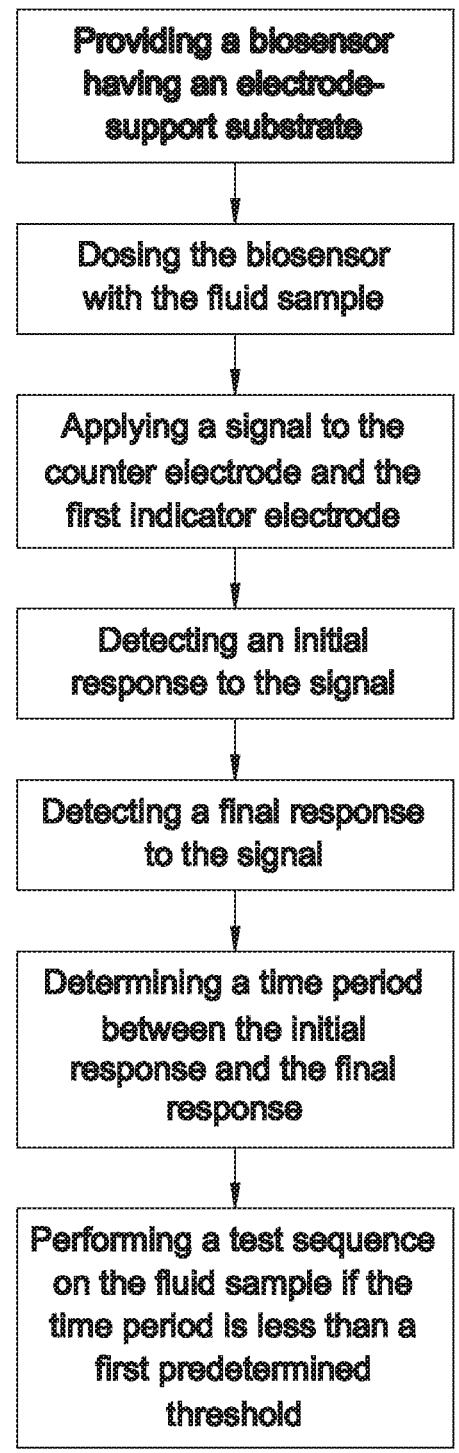
FIG. 6 is a flowchart of an alternative method of using the test element of FIG. 1 and having the electrode arrangement of FIG. 5.

FIG. 6 is a flowchart of one suitable method 300 of using the test element 10 having the electrode arrangement shown in FIG. 5. Prior to introducing the fluid sample to the capillary channel 26, the test meter or other device configured to use test element 10 applies a signal or test sequence 302, for example, without limitation, an AC signal and/or a DC signal, to the test element 10. In the method 300, the signal can be applied between each of the following electrode pairs: (1) the first counter electrode 60 and the working electrode 62, (2) the first counter electrode 60 and the first indicator electrode 64, (3) the first counter electrode 60 and the second indicator electrode 66, (4) the first working electrode 62 and the first indicator electrode 64, and/or (5) the first working electrode 62 and the first indicator electrode 66. The test element 10 is dosed 304 with the fluid sample from any one region of the open portions of the capillary channel 26, including the first end 46 or one of the opposite side edges 50, 52 causing the fluid sample to flow and fills across the capillary channel.

As the fluid sample fills across the capillary channel 26, the test meter monitors the above-described electrode pairs for continuity (i.e., a current flowing between the two electrodes, including between (1) the first counter electrode 60 and the working electrode 62, (2) the first counter electrode 60 and the first indicator electrode 64, and (3) the first counter electrode 60 and the second indicator electrode 66). In the method 300, the test meter monitors the three electrode pairs substantially simultaneously. Alternatively, the test meter can monitor the three electrode pairs sequentially such that only one of the three electrode pairs is monitored by the test meter during a specific period.

The test meter detects 306 an electric current between one or more of the first counter electrode 60 and the working electrode 62, the first counter electrode 60 and the first indicator electrode 64, and the first counter electrode 60 and the second indicator electrode 66, thereby indicating that the fluid sample has bridged or contacted at least a portion of the respective electrode pair. The test meter then continues to monitor the remaining electrode pairs to detect 308 an electric current. In this manner, the test meter can determine a fill direction of the capillary channel 26, and based on such fill direction, it can adjust or modify the analyte testing sequence or testing algorithm to accommodate for such fill direction. For example, without limitation, the test meter may first detect continuity between the first counter electrode 60 and the first indicator electrode 64, thereby indicating that the fluid sample entered from the side edge 52 of the capillary channel 26. Alternatively, the test meter may first detect continuity between the first counter electrode 60 and the working electrode 62, which can indicate that the fluid sample entered from the end edge 46 of the capillary channel 26. Thus, the sequence that the meter detects continuity between the three electrode pairs can give an indication of the fill direction of the capillary channels 26.

Subsequent to the continuity indications between the first counter electrode 60 and the working electrode 62, the first counter electrode 60 and the first indicator electrode 64, and the first counter electrode 60 and the second indicator electrode 66, the test meter determines 310 the time period between each of the continuity indications and compares each to predetermined thresholds. If the continuity indications occur after the predetermined thresholds, the test meter can provide an error alert to the user and instruct the user to try again using a new test element 10. However, if the continuity indications occur within the predetermined thresholds, the test meter executes 312 an analyte test sequence. Thus, the sequence of continuity indications and the respective measured time periods therebetween can be used as parameters to determine capillary channel 26 fill direction, inadequate fill volume, and/or dosing errors.

By monitoring the above-described electrode pairs (i.e., the first counter electrode 60 and the working electrode 62, the first counter electrode 60 and the first indicator electrode 64, and the first counter electrode 60 and the second indicator electrode 66, either substantially simultaneously or sequentially), the test meter can determine whether the test element 10 may have electrode defects, such as cracks, voids, etc. For example, if the test meter detects an electric current between either the first counter electrode 60 and the first indicator electrode 64 or the first counter electrode 60 and the second indicator electrode 66, indicating that the test element 10 is being dosed from one of the opposite side edges 50, 52, then the test meter logic would then expect to see the next continuity indication being between the first counter electrode 60 and the working electrode 62. However, if the test next detects an electric current between the first counter electrode 60 and the second indicator electrode 66, then such a detection sequence can indicate a problem such as, for example, an electrode defect, such as a crack or void in the working electrode 62, or trapped air bubbles that prevent progression of sample fill.

Moreover, after determining that the time period between each of the continuity indications occurred within the predetermined thresholds, as described above, the first and second indicator electrodes 64, 66 can either be disabled or converted to other functions. For example, in some instances, the first and second indicator electrodes 64, 66 are converted to additional counter electrodes to extend the effective surface area of the first counter electrode 60.

Generally, in an amperometric electrochemical measurement system, the surface area of the counter electrode is at least as large as the surface area of the working electrode for the counter electrode to not limit the current density of the measurement system. One advantage of increasing the effective surface area of the first counter electrode 60 by using the indicator electrodes 64, 66 is that the first working electrode 62 can be increased in size and the first counter electrode 60 and each of the two indicator electrodes 64, 66 can be sized such that their combined surface area is at least equal to that of the first working electrode. Because the current is proportional to the surface area of the first working electrode 62, having a larger surface area can improve the signal-to-noise ratio of the measurement system. Another advantage of increasing the effective surface area of the first counter electrode 60 by using the indicator electrodes 64, 66 is that the capillary channel 26 of the test element 10 can be decreased in size, thereby enabling a smaller fluid sample to be used, while still providing sufficient surface area of the working and counter electrodes for executing analyte measurements.

Alternatively, the first and second indicator electrodes 64, 66 can be converted to working electrodes. Generally, amperometric test elements function by the production of a current when a potential is applied between the counter and working electrodes. In the exemplary test element 10, the size of the capillary channel 26 and the surface area of the four co-planar electrodes 60, 62, 64, 66 are known. Accordingly, the test meter applies a potential between the first working electrode 62 and the first counter electrode 60 and records a current. The respective current density measurement (i.e., current/working electrode area). The test meter can use the measured current density between the first counter electrode 60 and the first working electrode 62 to predict current density measurements between the first counter electrode 60 and each of the indicator electrodes 64, 66. The current density measured at each indicator electrode 64, 66 should be substantially similar to the other indicator electrode's current density, assuming similar shapes and areas, and proportional to the current density of the primary electrode pair 60, 62. A large difference in the currents' ratio significantly different than the expected areas' ratio indicates an incomplete or irregular capillary fill. In some instances, an error message or failsafe can be displayed to a user.

Figure 7:
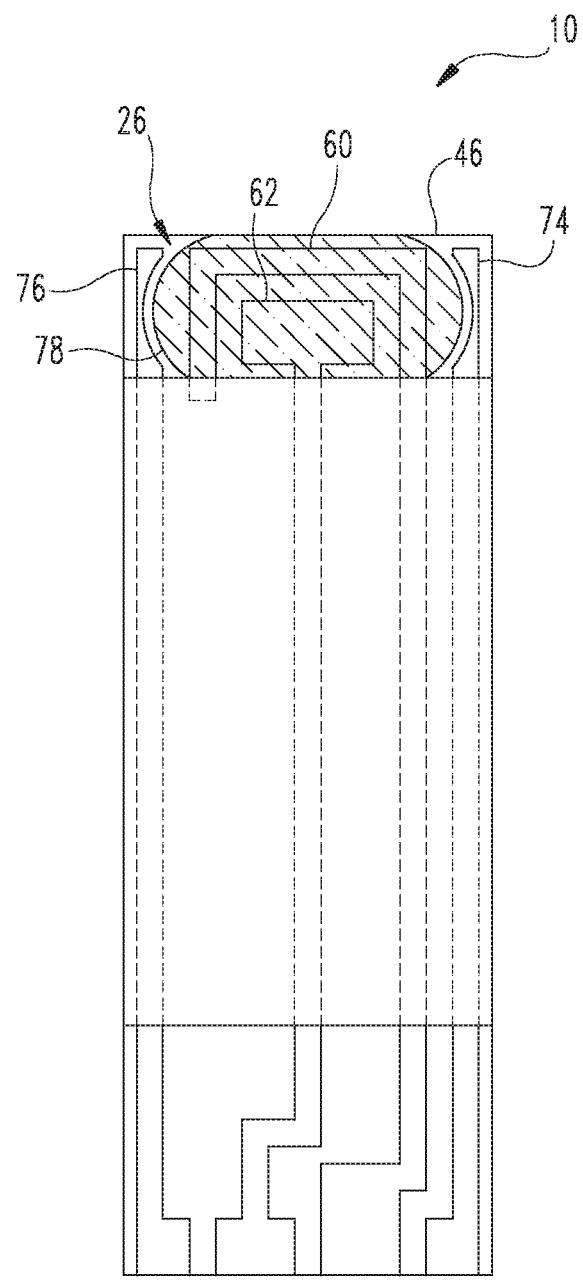
FIG. 7 is a plan view of an alternative electrode arrangement for use with the test element of FIG. 1.

FIG. 7 is a plan view of an alternative electrode arrangement for use with the test element shown in FIG. 1. The electrode arrangement is similar to the arrangement of FIG. 5; however, the two outer indicator electrodes 74 and 76 are shaped to imitate the anticipated fluid sample's flow front as the capillary channel 26 fills. Generally, the fluid sample enters the capillary channel 26 by capillary action and flows throughout the chamber providing a convex-shaped flow front 78 as shown in FIG. 7. Rectangular-shaped indicator electrodes 64, 66 (as shown in, e.g., FIG. 5) are not a preferred shape because they may falsely indicate a positive sample sufficiency by not accounting for the shape of the flow front 78 moving in the capillary channel 26. As such, indicator electrodes 74 and 76 each include a semi-circular inner edge that imitates the flow front 78. Alternatively, indicator electrodes 64, 66 may be shaped in any form that enables test element 10 to function as described herein. Shaping of the indicator electrodes 64, 66 to account for anticipated fluid flow front shape facilitates increasing the surface area available in the capillary channel 26 for the primary electrode pair 60, 62 facilitates reducing the percentage of the capillary channel that needs to be filled to be sufficient, and facilitates reducing the chance of an incorrect sample volume indication. Fluid flow fronts will vary with the analyte matrix, as well as surface properties of the capillary channel, so the end design will depend on these parameters.

FIGS. 8-12 are plan views of alternative capillary channels 26 for use with the test element 10 shown in FIG. 1. Shown are FWED structures that facilitate users targeting corners or central portions of the test element 10 for dosing. In general, narrower portions of the capillary channel 26 structure facilitates fill performance by facilitating breaking the surface tension of a drop of the fluid sample to be applied to the test element. Furthermore, each of the embodiments shown in FIGS. 8-12 have an additional benefit of reducing the fluid sample volume necessary to adequately cover the measurement electrodes and fill the capillary channel 26.

Figure 8:
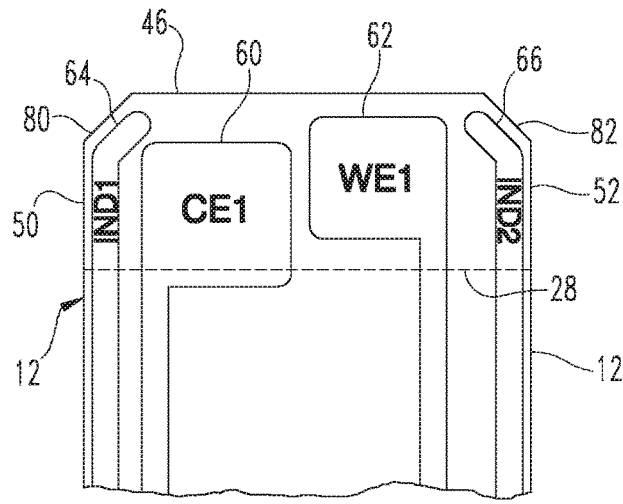
FIG. 8 is a plan view of an alternative capillary channel for use with the test element of FIG. 1.

FIG. 8 is a plan view of an alternative capillary channel 26 for use with the test element 10 shown in FIG. 1. Here, the electrode-support substrate 12 includes two chamfer portions 80, 82 extending between the end edge 46 and the opposite side edges 50, 52, respectively. Chamfer portions 80, 82 are sized to account for the specific fluid sample that the test element is intended to measure (e.g., blood, urine, etc.). Further, chamfer portions 80, 82 can be formed at any angle that enables the capillary channel 26 to function as described herein. The chamfers create additional corners or edges to facilitate breaking surface tension to help fill the capillary channel. The indicator electrodes 64, 66 can be co-function electrodes and function as indicator electrode and either counter electrode or working electrodes as described above. While the chamfer portions 80, 82 facilitate entry of the fluid sample into the capillary channel 26, the entry point of the fluid sample can be any location along the capillary channel. The indicator electrodes 64, 66 are arranged within the capillary channel 26 to monitor fill direction and adequate fill time of the capillary channel.

Figure 9:
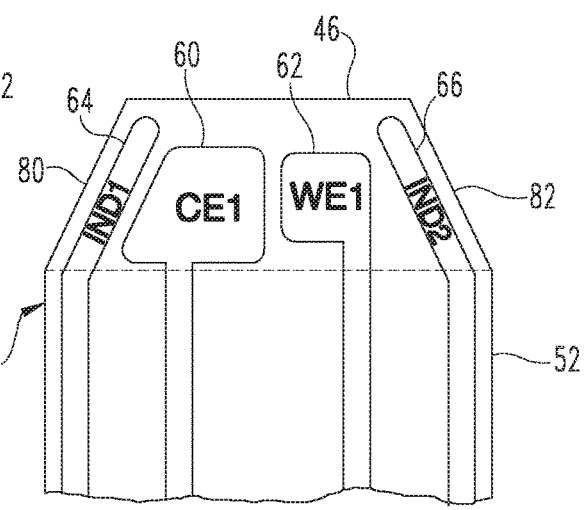
FIG. 9 is a plan view of an alternative capillary channel for use with the test element of FIG. 1.

FIG. 9 is a plan view of an alternative capillary channel 26 for use with the test element 10 shown in FIG. 1. FIG. 9 is similar to FIG. 8 in that it includes chamfer portions 80, 82. However, in FIG. 9 chamfer portions 80, 82 each extend from the respective opposite side edges 50, 52 at the intersection point of the end edge 28 of the spacer 23. Thus, the capillary channel 26 is defined by the open end edge 46, chamfer portions 80, 82, and the end edge 28 of spacer 23. Advantageously, chamfer portions create additional corners and/or edges to facilitate breaking surface tension to help fill the capillary channel.

Figure 10:
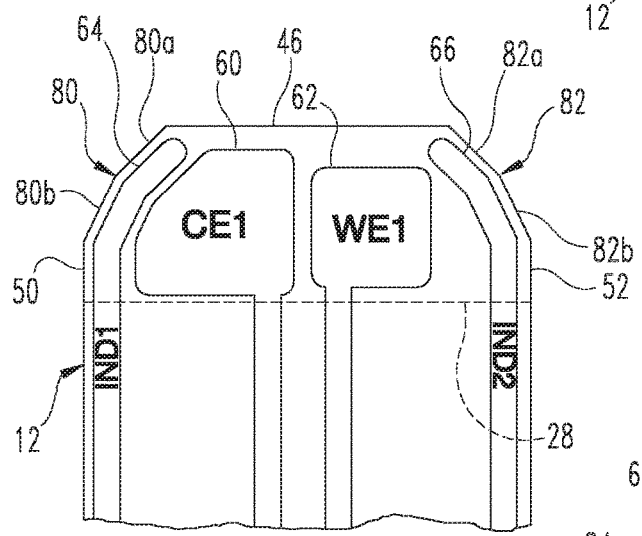
FIG. 10 is a plan view of an alternative capillary channel for use with the test element of FIG. 1.

FIG. 10 is a plan view of an alternative capillary channel 26 for use with the test element 10 shown in FIG. 1. Here, the chamfer portions 80, 82 include two or more segments. For example, chamfer portion 80 is shown having two segments 80a, 80b. In addition, chamfer portion 82 is shown having two segments 82a, 82b, which are substantially symmetric to segments 80a, 80b. As such, segments 80a, 80b, 82a, 82b facilitate improving fill performance by providing additional narrow sections and corners to capillary channel 26, thereby facilitating breaking the surface tension of the fluid sample and allowing efficient filling of the capillary channel.

Figure 11:
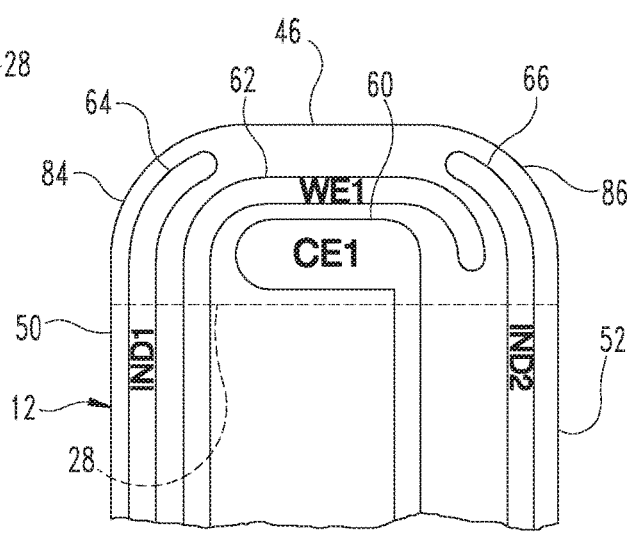
FIG. 11 is a plan view of an alternative capillary channel for use with the test element of FIG. 1.

FIG. 11 is a plan view of an alternative capillary channel 26 for use with the test element 10 shown in FIG. 1. Here, the electrode-support substrate 12 includes a curved portion 84 extending between end edge 46 and side edge 50, and a curved portion 86 extending between end edge 46 and side edge 52. Curved portions 84, 86 are sized to account for the specific fluid sample that the test element is intended to measure (e.g., blood, urine, etc.). Further, curved portions 84, 86 can have any radius, or varying radius, that enables the capillary channel 26 to function as described herein. As described above, the indicator electrodes 64, 66 can be co-function electrodes and function as indicator electrode and either counter electrode or working electrodes as described above. The indicator electrodes 64, 66 are arranged within the capillary channel 26 to monitor fill direction and adequate fill time of the capillary channel.

Figure 12:
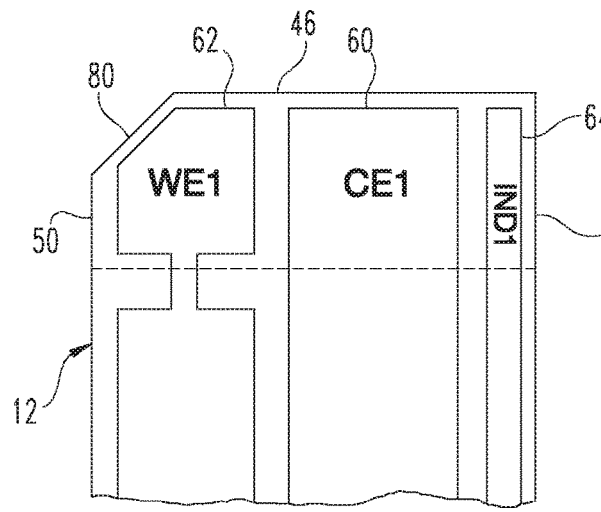
FIG. 12 is a plan view of an alternative capillary channel for use with the test element of FIG. 1.

FIG. 12 is a plan view of an alternative capillary channel 26 for use with the test element 10 shown in FIG. 1. Here, the electrode-support substrate 12 includes a single chamfer portion 80 extending between the end edge 46 and the side edge 50. Chamfer portion 80 is sized to account for the specific fluid sample that the test element is intended to measure (e.g., blood, urine, etc.). Further, chamfer portion 80 can be formed at any angle that enables the capillary channel 26 to function as described herein. A single indicator electrode 64 is shown and can be co-function electrode that functions as an indicator electrode and either a counter electrode or a working electrode as described above. This asymmetrical design of test element 10 facilitates encouraging a user to dose the test element at chamfer 80, thereby facilitating improving fill performance, and enabling efficient filling of the capillary channel.

Figure 13:
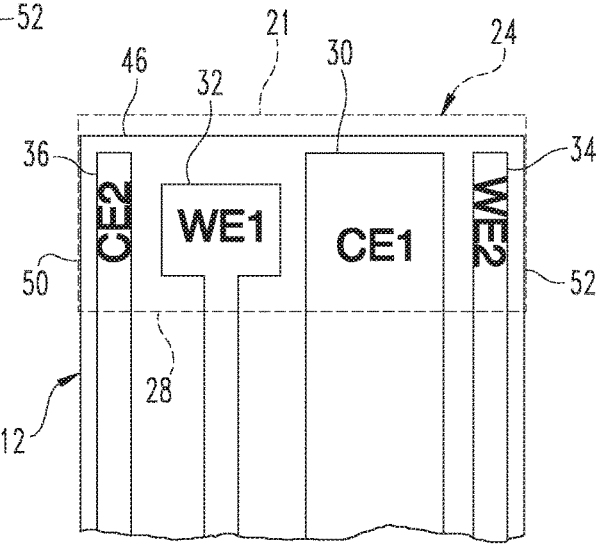
FIG. 13 is a plan view of a portion of the test element of FIG. 1 showing an exemplary cover.
Figure 14:
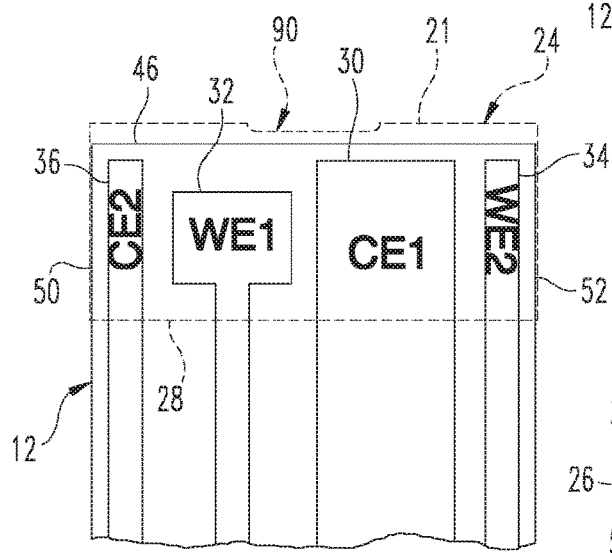
FIG. 14 is a plan view of a portion of the test element of FIG. 1 showing an alternative cover.

FIGS. 13-17 are plan views of a portion of the test element 10 shown in FIG. 1 showing several arrangements for the cover 24. FIG. 13 shows the cover 24 having a substantially straight end 21 that extends a predetermined distance beyond the first end 46 of the electrode-support substrate 12, thereby providing a cantilever based capillary channel 26 (see, e.g., FIG. 2). A hydrophobic layer on the cover can facilitate breaking surface tension of a drop of the sample and help fill the capillary channel. FIG. 14 shows the cover 24 including a discontinuity, or a single rectangular-shaped notch 90 to facilitate target dosing of test element 10. The notch 90 is formed in the end 21 of the cover 24, and in particular, in the portion of the cover that overhangs the electrode-support substrate 12 (i.e., the notch 90 extends a predefined distance away from the end 21, but before it reaches the end 46 of the electrode-support substrate 12). As such, the notch 90 is substantially centered on the cover 24 to facilitate targeting center dosing of the test element 10. Alternatively, the notch 90 can be positioned anywhere along the end 21 of the cover such that the test element 10 functions as described herein.

Figure 15:
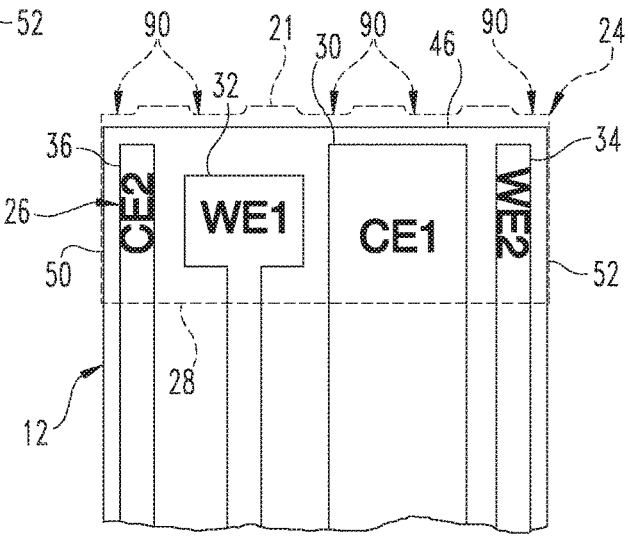
FIG. 15 is a plan view of a portion of the test element of FIG. 1 showing an alternative cover.

FIG. 15 shows the cover 24 including a series of rectangular-shaped notches 90 to facilitate providing a discontinuous end 21 of the cover 24. The abrupt discontinuities of end 21 provided by notches 90 facilitates breaking the surface tension of the fluid sample and enables efficient filling of the capillary channel 26 of the test element 10. The notches 90 are formed in the end 21 of the cover 24, and in particular, in the portion of the cover that overhangs the electrode-support substrate 12 (i.e., the notches 90 extend a predefined distance away from the end 21, but terminate before they reach the end 46 of the electrode-support substrate 12).

Figure 16:
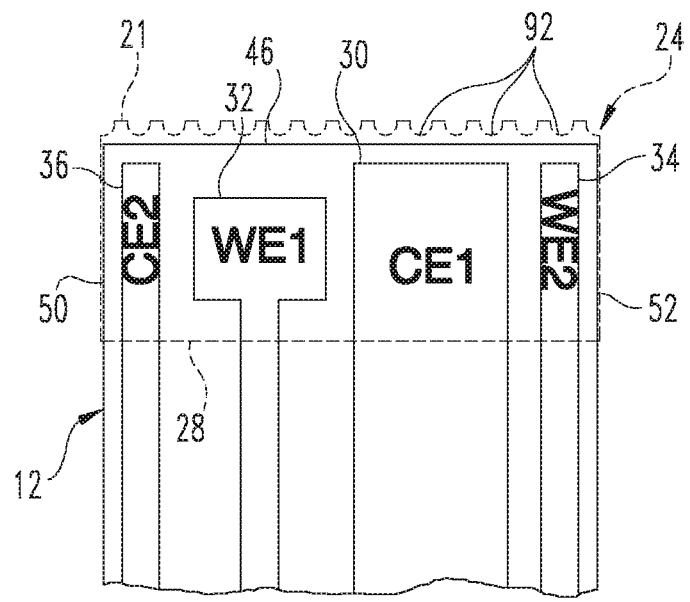
FIG. 16 is a plan view of a portion of the test element of FIG. 1 showing an alternative cover.
Figure 17:
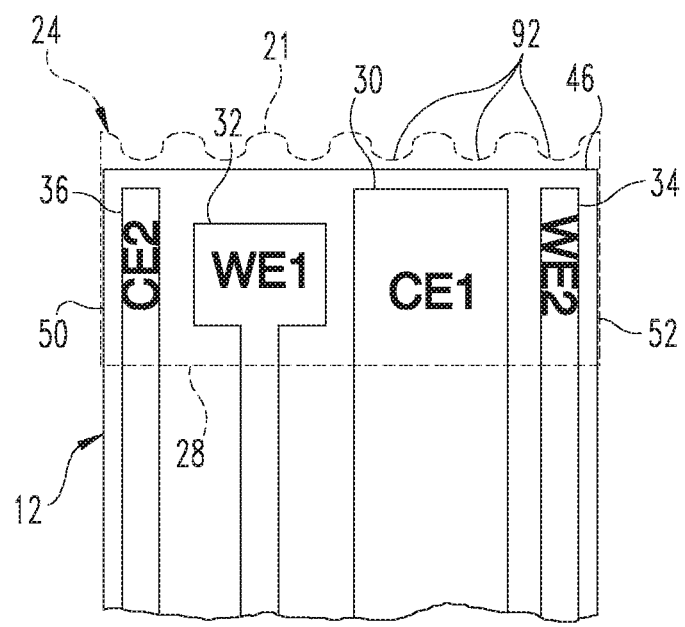
FIG. 17 is a plan view of a portion of the test element of FIG. 1 showing an alternative cover.
Figure 18:
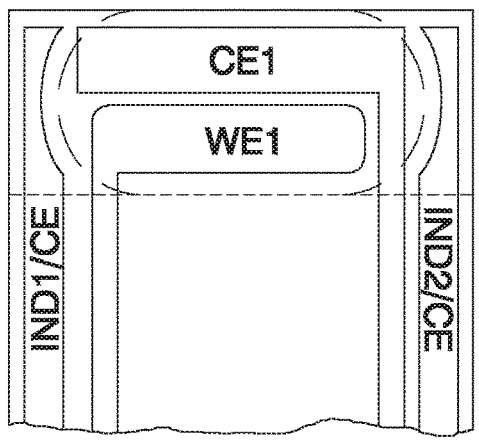
FIGS. 18-23 show various diagrams of convex sample flow (left column.
Figure 19:
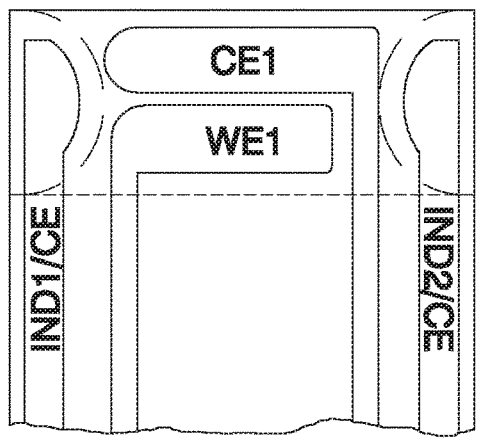
Figure 20:
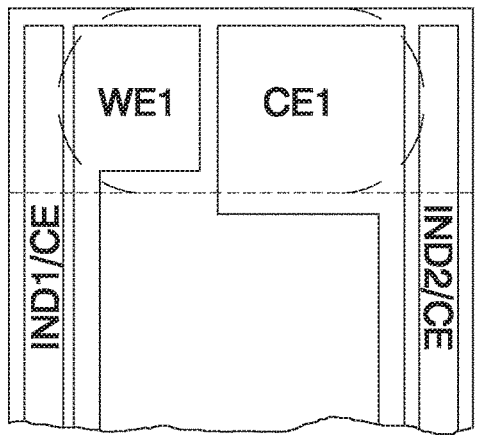
Figure 21:
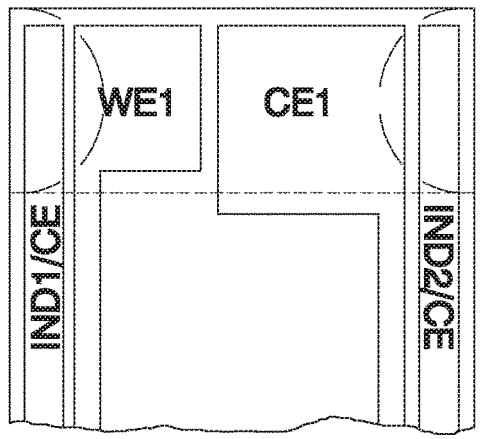
Figure 22:
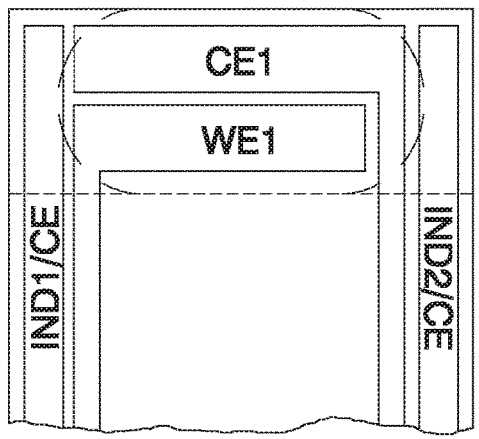
Figure 23:
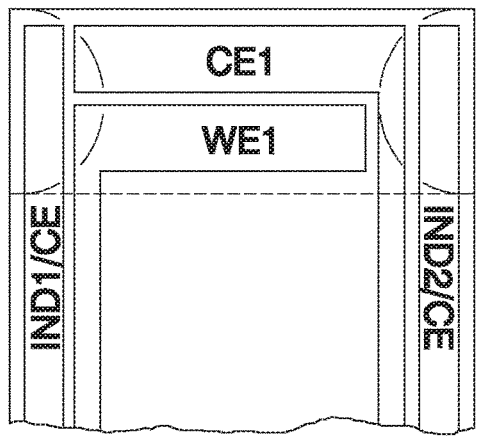

FIG. 16 shows the cover 24 including a series of semicircular shaped cutouts 92 to facilitate providing a discontinuous end 21 of the cover 24. The abrupt discontinuities of end 21 provided by cutouts 92 facilitates breaking the surface tension of the fluid sample and enables efficient filling of the capillary channel 26 of the test element 10. The cutouts 92 are formed in the end 21 of the cover 24, and in particular, in the portion of the cover that overhangs the electrode-support substrate 12 (i.e., the cutouts 92 extend a predefined distance away from the end 21, but terminate before they reach the end 46 of the electrode-support substrate 12). Alternatively, the cutouts 92 can include rounded corners as shown in FIG. 17 to provide a smoother edge 21 to the cover 24, while still facilitating breaking the surface tension of the fluid sample and enabling efficient filling of the capillary channel 26.

All of the patents, patent applications, patent application publications and other publications recited herein are hereby incorporated by reference as if set forth in their entirety.

The present inventive concept has been described in connection with what are presently considered to be the most practical and preferred embodiments. However, the inventive concept has been presented by way of illustration and is not intended to be limited to the disclosed embodiments. Accordingly, one of skill in the art will realize that the inventive concept is intended to encompass all modifications and alternative arrangements within the spirit and scope of the inventive concept as set forth in the appended claims.

LISTING OF REFERENCE NUMBERS 10 test element
12 electrode-support substrate
14 electrical conductor
16 electrode trace
18 electrode trace
20 electrode trace
21 end
22 electrode trace
23 spacer
24 cover
25 inner surface
26 capillary channel
27 lower surface
28 end edge
29 upper surface
30 electrode 31 hydrophilic coating
32 electrode
33 hydrophobic coating
34 electrode
36 electrode
42 first surface
44 second surface
46 first end
48 second end
50 side edge
52 opposing side edge
60 electrode
62 electrode
64 electrode
66 electrode
74 indicator electrode
76 indicator electrode
78 fluid flow front
80 chamfer portion
82 chamfer portion
84 curved portion
86 curved portion
90 notch
92 semi-circular shaped cutout(s)
200 method
202 test meter
204 dosing step
206 detecting step
208 detecting step
210 determining step
212 analyte test sequence executing step
300 method
302 signal or test sequence
304 dosing step
306 detecting step
308 detecting step
310 determining step
312 analyte test sequence executing step

The invention claimed is:

1. A test element comprising:
an electrode-support substrate comprising a capillary channel defined thereon at a first end of the electrode-support substrate, the electrode-support substrate further comprising a first side edge and a second side edge, the first end forming a continuous edge between the first side edge and the second side edge;
a spacer positioned on the electrode-support substrate, the spacer comprising a continuous end edge defining a boundary of the capillary channel, wherein the first end of the electrode-support substrate is offset from and extends a first predetermined distance beyond the end edge of the spacer;
a first electrode pair provided within the capillary channel on the electrode-support substrate, the first electrode pair including a first counter electrode and a first working electrode;
a first and a second indicator electrode provided within the capillary channel on the electrode-support substrate, each of the first and second indicator electrodes being positioned along a respective side edge of the electrode-support substrate, wherein the first electrode pair is positioned between the first and second indicator electrodes, and wherein each of a first end of the first indicator electrode and a first end of the second indicator electrode is shaped with a semi-circular inner edge indentation to detect a convex fluid flow into the capillary channel;
a reagent composition for an analyte of interest disposed over at least the first electrode pair; and
a cover coupled to the spacer, the cover comprising a cover first end, a first side edge, and a second side edge that substantially correspond to the first side edge and the second side edge of the electrode-support substrate, respectively, wherein at least the cover first end is offset from and extends a second predetermined distance beyond the first end of the electrode-support substrate, defining an overhang portion, and the cover is offset from and extends a third predetermined distance beyond the end edge of the spacer, the cover further comprising at least one discontinuity formed in the first end, the discontinuity being entirely within the overhang portion.

2. The test element of claim 1, wherein the at least one discontinuity formed in the overhang portion comprises at least one rectangular-shaped notch to facilitate targeting dosing of the test element.

3. The test element of claim 2, wherein the at least one rectangular-shaped notch comprises a plurality of notches spaced between the first and second side edges of the cover.

4. The test element of claim 1, wherein the at least one discontinuity formed in the overhang portion comprises a plurality of semi-circular shaped cutouts spaced between the first and second side edges of the cover.

5. The test element of claim 4, wherein each one of the plurality of semi-circular shaped cutouts comprises rounded corners.

* * * * *